US011642307B2

(12) United States Patent
Navarro (10) Patent No.: US 11,642,307 B2
(45) Date of Patent: May 9, 2023

(54) AMBRISENTAN FOR USE IN THE TREATMENT OF ACUTE RENAL FAILURE

(71) Applicant: Noorik Biopharmaceuticals AG, Basel (CH)

(72) Inventor: Iker Navarro, Riehen (CH)

(73) Assignee: Noorik Biopharmaceuticals AG, Basel (CH)

(*) Notice: Subject to any disclaimer, the term of this patent is extended or adjusted under 35 U.S.C. 154(b) by 343 days.

(21) Appl. No.: 17/065,097

(22) Filed: Oct. 7, 2020

(65) Prior Publication Data

US 2021/0046332 A1 Feb. 18, 2021

Related U.S. Application Data (62) Division of application No. 16/084,340, filed as application No. PCT/EP2017/056476 on Mar. 20, 2017, now Pat. No. 10,870,021.

(60) Provisional application No. 62/437,949, filed on Dec. 22, 2016, provisional application No. 62/310,221, filed on Mar. 18, 2016.

(30) Foreign Application Priority Data

Apr. 19, 2016 (EP) .................................. 16166046

(51) Int. Cl.
| | | |
|---|---|---|
| *A61K 31/505* | (2006.01) | |
| *A61P 13/12* | (2006.01) | |
| *A61K 9/00* | (2006.01) | |
| *A61K 9/08* | (2006.01) | |
| *A61K 31/00* | (2006.01) | |
| *G01N 33/70* | (2006.01) | |

(52) U.S. Cl.
CPC ............. *A61K 9/0019* (2013.01); *A61K 9/00* (2013.01); *A61K 9/08* (2013.01); *A61K 31/505* (2013.01); *A61P 13/12* (2018.01); *A61K 31/00* (2013.01); *G01N 33/70* (2013.01)

(58) Field of Classification Search
CPC ............................. A61P 13/12; A61K 31/505
See application file for complete search history.

(56) References Cited

U.S. PATENT DOCUMENTS

| | | |
|---|---|---|
| 7,601,730 B2 | 10/2009 | Riechers et al. |
| 2010/0204163 A1 | 8/2010 | Melvin |
| 2011/0319333 A1 | 12/2011 | Newman et al. |
| 2013/0252898 A1 | 9/2013 | Newman et al. |
| 2015/0125546 A1 | 5/2015 | Belardinelli et al. |

FOREIGN PATENT DOCUMENTS

WO 2014/138738 9/2014

OTHER PUBLICATIONS

International Search Report dated May 30, 2017 in International (PCT) Application No. PCT/EP2017/056476.
International Preliminary Report on Patentability dated Sep. 18, 2018 in International (PCT) Application No. PCT/EP2017/056476.
Raina et al., "The Pathophysiology of Endothelin in Complications After Solid Organ Transplantation: A Potential Novel Therapeutic Role for Endothelin Receptor Antagonists", Transplantation, vol. 94, No. 9, pp. 885-893, 2012.
Zhang et al., "Ambrisentan improves the outcome of rats with liver transplantation partially through reducing nephrotoxicity", European Review for Medical and Pharmacological Sciences, vol. 18, No. 17, pp. 2575-2583, 2014.
Anand et al., "Endothelin is an important determinant of renal function in a rat model of acute liver and renal failure", Gut, vol. 50, pp. 111-117, 2002.
Braun et al., "Prevention of Chronic Renal Allograft Rejection in Rats With an Oral Endothelin a Receptor Antagonist", Transplantation, vol. 68, No. 6, pp. 739-746, 1999.
Braun et al., "Improved recovery following postuansplant acute renal failure in rat renal isografts with an oral endothelin-A receptor antagonist", Experimental Nephrology, vol. 8, No. 4-5, pp. 283-290, 2000, Abstract.
Herrero et al., "Prevention of cold ischaemia-reperfusion injury by an endothelin receptor antagonist in experimental renal transplantation", Nephrology Dialysis Transplantation, vol. 14, pp. 872-880, 1999.
Knoll et al., "Therapeutic administration of an endothelin-A receptor antagonist after acute ischemic renal failure dose-dependently improves recovery of renal function", Journal of Cardiovascular Pharmacology, vol. 37, No. 4, pp. 483-488, 2001, Abstract.
Knoll et al., "Influence of acute selective endothelin-receptor-A blockade on renal hemodynamics in a rat model of chronic allograft rejection", Transplant International, vol. 16, No. 6, pp. 425-429, 2003.
Soper et al. "Amelioration of hepatorenal syndrome with selective endothelin-A antagonist", The Lancet, vol. 347, pp. 1842-1843, 1996.
Wei et al. "Clinical Adverse Effects of Endothelin Receptor Antagonists: Insights From the Meta-Analysis of 4894 Patients From 24 Randomized Double-Blind Placebo-Controlled Clinical Trials", Journal of the American Heart Association, vol. 5, No. 11, e:003896, 2016.
Moreno et al., "Portal blood flow in cirrhosis of the liver," Journal of Clinical Investigation, vol. 46, No. 3, pp. 436-445, 1967.
Bosch et al., "The clinical use of HVPG measurements in chronic liver disease", Nature Reviews Gastroenterology & Hepatology, vol. 6, No. 10, pp. 573-582, 2009.
Moore, "Endothelin and vascular function in liver disease", Gut, vol. 53, No. 2, pp. 159-161, 2004.

(Continued)

Primary Examiner — Jeffrey S Lundgren
Assistant Examiner — Chris E Simmons
(74) Attorney, Agent, or Firm — Wenderoth, Lind & Ponack, L.L.P.

(57) ABSTRACT

Ambrisentan and formulations thereof for use in the treatment and prevention of acute renal failure associated with renal vasoconstriction.

16 Claims, 1 Drawing Sheet

(56) References Cited

OTHER PUBLICATIONS

Moore et al., "Plasma endothelin immunoreactivity in liver disease and the hepatorenal syndrome", The New England Journal of Medicine, vol. 327, No. 25, pp. 1774-1778, 1992.
Pitts, "Endothelin receptor antagonism in portal hypertension", Expert Opinion on Investigational Drugs, vol. 18, No. 2, pp. 135-142, 2009.
Tripathi et al., "Endothelin-1 contributes to maintenance of systemic but not portal haemodynamics in patients with early cirrhosis: a randomised controlled trial.," Gut, vol. 55, No. 9, pp. 1290-1295, 2006.
Zipprich et al., "Selective Endothelin-A-Blocker decrease portal pressure in patients with cirrhosis. A feasibility study combining the local intraarterial and systemic administration," Z. Gastroenterologie, vol. 54, No. 12, pp. 1343-1404, 2016, Congress Abstract.
Halank et al., "Ambrisentan improves exercise capacity and symptoms in patients with portopulmonary hypertension," Z. Gastroenterologie, vol. 49, No. 9, pp. 1258-1262, 2011.
Savale et al., "Efficacy, safety and pharmacokinetics of bosentan in portopulmonary hypertension," European Respiratpory Journal, vol. 41, No. 1, pp. 96-103, 2013.
Hoeper et al., "Experience with inhaled iloprost and bosentan in portopulmonary hypertension", European Respiratory Journal, vol. 30, No. 6, pp. 1096-1102, 2007.
Kähler et al., "Successful treatment of portopulmonary hypertension with the selective endothelin receptor antagonist Sitaxentan.," Wiener klinische Wochenschrift The Central European Journal of Medicine, vol. 123, No. 7-8, pp. 248-252, 2011.
Muraoka et al., "Secure Combination Therapy With Low-Dose Bosentan and Ambrisentan to Treat Portopulmonary Hypertension Minimizing Each Adverse Effect.," International Heart Journal, vol. 56, No. 4, pp. 471-473, 2015.
Yamashita et al., "Hemodynamic effects of ambrisentan-tadalafil combination therapy on progressive portopulmonary hypertension", World Journal of Hepatology, vol. 6, No. 11, pp. 825-829, 2014.
Hinterhuber et al., "Endothelin-receptor antagonist treatment of portopulmonary hypertension," Clinical Gastroenterology and Hepatology, vol. 2, No. 11, pp. 1039-1042, 2004.
Clinical Study, NCT01224210, "Ambrisentan in Patients With Porto-pulmonary Hypertension A Multicenter Open Label Trial (Portopulm)" Tufts Medical Center, 2010.
Clinical Study, NCT02382016, "PORtopulmonary Hypertension Treatment with maCitentan—a randOmized Clinical Trial (PORTICO)", Actelion, 2015.
Shih et al., "Portal vein pulsatility index is a more important indicator than congestion index in the clinical evaluation of right heart function", World Journal of Gastroenterology, vol. 12, No. 5, pp. 768-771, 2006.
Angus, "Role of endothelin in systemic and portal resistance in cirrhosis", Gut, vol. 55, No. 9, pp. 1230-1232, 2006.
Krowka et al., "Efficacy and Safety of Macitentan in Patients with Portopulmonary Hypertension: The Randomized, Placebo Controlled Portico Trial", Hepatology, AASLD Abstracts, 70A, 2018.
Wong et al., "Lack of Renal Improvement with Nonselective Endothelin Antagonism with Tezosentan in Type 2 Hepatorenal Syndrome", Hepatology, vol. 47, No. 1, pp. 160-168, 2008.
Lebrec et al., "Hemodynamic Effects of Tezosentan, a Dual Endothelin Receptor Antagonist, in Patients With Cirrhosis", Journal of Hepatology, vol. 52, p. S210, 2010.
Soper C.P.R. et al., "The Renal Haemodynamic Response to BQ123 in Hepatorenal Syndrome", SW Thames Renal Unit, St. Helier Hospital London, 127.
Acute kidney failure, Mayo Clinic, Jun. 23, 2018, available at: http://www.mayoclinic.org/diseases-conditions/kidney-failure/basics/definition/con-20024029.
Battistini et al., "Profile of Past and Current Clinical Trials Involving Endothelin Receptor Antagonists: The Novel '-Sentan' Class of Drug", Exp Biol Med, vol. 231, pp. 653-695 (2006).
Moreland, "BQ-123, A Selective Endothelin ETA Receptor Antagonist", Cardiovascular Drug Reviews, vol. 12, No. 1, pp. 48-69 (1994).
Mann et al., "Avosentan for Overt Diabetic Nephropathy", J Am Soc Nephrol, vol. 21, pp. 527-535 (2010).
Lebrec et al., "Hemodynamics and pharmacokinetics of tezosentan, a dual endothelin receptor antagonist, in patients with cirrhosis", Eur J Clin Pharmacol, vol. 68, pp. 533-541 (2012).
Chin et al., "Effects of tezosentan, a dual endothelin receptor antagonist, on the cardiovascular and renal systems of neonatal piglets", Journal of Pediatric Surgery, vol. 36, issue 12, pp. 1824-1828 (Dec. 2001), Abstract.
Enevoldsen et al., "Endothelin Receptor Antagonists: Status Quo and Future Perspectives for Targeted Therapy", Journal of Clinical Medicine, vol. 9, issue 3, 824, pp. 1-29 (2020).
Moore et al., ("Guidelines on the management of ascites in cirrhosis." Gut. Oct. 2006; 55 (Suppl 6): vi1-vi12). (Year: 2006).
Gerbes et al. (Digestion. Jul. 1998;59 Suppl 2:8-10). (Year: 1998).
Goddard et al. (Circulation. 2004;109:1186-1193). (Year: 2004).

AMBRISENTAN FOR USE IN THE TREATMENT OF ACUTE RENAL FAILURE

CROSS-REFERENCE TO RELATED APPLICATIONS

The present application is divisional application of U.S. application Ser. No. 16/084,340 filed Sep. 12, 2018, which is a national stage application filed under 35 U.S.C. § 371 of international application no. PCT/EP2017/056476 filed Mar. 20, 2017, which claims the benefit of U.S. Provisional Application No. 62/437,949 filed Dec. 22, 2016 and U.S. Provisional Application No. 62/310,221 filed Mar. 18, 2016, and claims priority to European Patent Application No. 16166046.9 filed Apr. 19, 2016, the entirety of each of which is incorporated herein by reference.

FIELD

This invention relates to the treatment, prevention of acute renal failure associated with renal vasoconstriction and to related therapeutic and prophylactic formulations. The invention further pertains to the identification of reduced renal function due to vasoconstriction, and to formulations suitable for such identification.

BACKGROUND

Acute renal failure is a life-threatening condition that occurs when the kidneys are suddenly unable to filter waste products from the blood. Also known as acute kidney failure or acute kidney injury, this condition can develop over a few hours or even a few days. Most commonly, it affects people who are already hospitalized, particularly those who are critically ill. See, for example a report by the Mayo Clinic about kidney failure (http://www.mayoclinic.org/diseases-conditions/kidney-failure/basics/definition/con-20024029).

Various signs and symptoms of acute renal failure include decreased urine output, although occasionally urine output remains normal; fluid retention, which causes swelling in the legs, ankles or feet; drowsiness; shortness of breath; fatigue; confusion; nausea; seizures or coma in severe cases; and chest pain or pressure. However, some patients have no signs or symptoms and this condition is detected through laboratory tests done for other reasons. Regardless of the particular symptoms that may be present, the mortality of acute renal failure has been estimated at up to 50% or more.

Acute renal failure can occur as a result of having a condition that slows blood flow to the kidney, when the kidneys suffer direct damage or when the ureters, which are the kidneys' draining tubes, become blocked. It is also caused by conditions that severely increase renal vascular resistance leading to insufficient renal blood flow, secondary to an increase in endothelin (ET), in which renal vasoconstriction causes a substantial decrease of blood flow to the kidneys.

Endothelin is a naturally occurring peptide found in blood plasma. It has two known receptors, that is the endothelin A receptor (ETR-A) and the endothelin B receptor (ETR-B). The ETR-A is capable of mediating an increase in vascular tone and is typically found in the smooth muscle tissue in blood vessels. Binding of endothelin to the ETR-A leads to vasoconstriction. The ETR-B plays a role in the vascular tone as well mediating vasodilation. In addition, the endothelin B receptor is present in the renal tubules and collecting ducts and participates in diuresis. The ETR-B also acts as a clearance receptor for endothelin.

Types of acute renal failure associated with renal vasoconstriction caused by endothelin include, for example, Hepatorenal Disorders such as Hepatorenal Syndrome (HRS), Refractory Ascites and Dilutional Hyponatremia. Other disorders associated with renal vasoconstriction caused by endothelin include, for example, Delayed Graft Function (DGF), Calcineurin-Inhibitor Nephrotoxicity (CNI), Contrast-Induced Acute Kidney Injury (CIAKI), Cardiorenal Syndrome (CS) and Acute Kidney Injury following Cardiac Surgery (AKICS).

Hepatorenal Disorders refers to a condition characterized by the presence of renal insufficiency in a subject with liver failure (for example, cirrhosis with or without ascites, acute liver failure, and the like). Such Hepatorenal Disorders include HRS, Refractory Ascites and Dilutional Hyponatremia. HRS is a disease with a high mortality (Type I HRS of up to 50% in 2 weeks), and the probability of survival is very low. Hepatorenal Disorders occur in patients, that have advanced liver disease and in general have no previous history of renal disease, and is characterized by extreme renal vasoconstriction. A notable clinical feature is a rapidly progressive renal failure that is refractory to conventional treatment, such as with fluid resuscitation and/or the use of diuretics. There is no specific, effective treatment available for this condition. In such cases, liver transplantation is generally considered, and a recovery of liver function may subsequently correct and improve renal function. In some instances, however, simultaneous liver and kidney transplantation are performed, as it is generally difficult to assess whether renal failure is functional (i.e. reversible and secondary to renal vasoconstriction induced by liver failure) or not. If renal failure is not functional in nature, simultaneous liver and kidney transplantations are preferred. Refractory Ascites and Dilutional Hyponatremia are renal complications observed in patients with advanced liver disease characterized by intense renal vasoconstriction and secondary to avid sodium and water reabsorption by the kidney. The main clinical characteristic of Refractory Ascites is the inability to use diuretics or the decreased efficacy of diuretics in the treatment of recurrent ascites, which results in the frequent need for paracentesis. Dilutional Hyponatremia is a metabolic abnormality which is characterized by an increased retention of water and a dilutional state, resulting in low serum sodium concentrations.

Delayed Graft Function (DGF) is a complication of renal transplantation, occurring most frequently in transplanted kidneys originating from deceased donors or donors of extended criteria (for example, older donors, donors with hypertension or donors with a high terminal serum creatinine, among others). DGF is rare with living donor kidney transplants. DGF can complicate the post-operative course in 20-40% of the cases and there is no treatment for this condition. Clinically, DGF manifests itself as a low or non-functioning kidney following transplantation. It is characterized by higher endothelin levels, lower glomerular filtration rate and an increase in renal vascular resistance.

Contrast-Induced Acute Kidney Injury (CIAKI), also known as Contrast-Induced Nephropathy, is a renal complication following the administration of iodine-based radiological contrast media, occurring most frequently in subjects with pre-existing renal failure, older subjects or subjects treated with large amounts of contrast media. CIAKI is characterized by an increase in renal vascular resistance and a decrease in glomerular filtration rate, the latter reflected as an increase in serum creatinine.

Cardiorenal Syndrome (CS) is a common renal complication occurring in patients with heart failure and is clinically characterized by the retention of water and sodium and a decrease in glomerular filtration rate. Some forms of CS are characterized by an increase in renal vascular resistance, decreased renal blood flow, low urinary and sodium output and respond poorly to diuretic treatment.

Acute Kidney Injury following Cardiac Surgery (AKICS) is a complication occurring in the immediate post-operative period of subjects undergoing complex cardiac surgery. It is characterized by an increase in renal vascular resistance, decreased renal blood flow and a decrease in glomerular filtration rate.

Calcineurin Inhibitor Nephrotoxicity (CNI) refers to an acute or chronic, and initially reversible renal deficit associated to the use of calcineurin inhibitors, such as cyclosporine A or tacrolimus. In its acute form, CNI is characterized by renal vasoconstriction leading to a reduction in glomerular filtration rate and predominantly impaired renal tubular function. In its chronic form, renal hemodynamic changes are present in addition to other fibrotic, hyperplastic and vascular changes in the kidney, such as interstitial fibrosis, tubular atrophy, glomerular fibrosis and arterial hyalinosis. CNI is believed to be secondary to the upregulation of endothelin, activation of the renin-angiotensin-aldosterone system and ensuing chronic ischemia of the kidney. Clinically, the disease is characterized by increased systemic blood pressure, electrolyte disturbances and hyperuricemia.

In Raina et al (in Transplant. J., vol. 94, no. 9, 2012, pp. 885-893), a series of experiments in animals and humans are summarized and which support the potential role of ambrisentan to counter the effects of calcineurin inhibitors following renal transplantation. The dose of ambrisentan referred to and used in the human studies is 5 and 10 mg/day which leads to plasma levels exceeding 350 ng/ml. The authors refer to the absence of pharmacokinetic interactions between ambrisentan and cyclosporine A and tacrolimus as a further basis for the role of ambrisentan in preventing calcineurin-inhibitor nephrotoxicity.

In a further article by Zhang et al (in European review for medical & pharmacological science, 2014, 18, pp. 2575-2583) results obtained with the co-administration of tacrolimus and ambrisentan in rats show that ambrisentan can counter the renal toxicity of tacrolimus, at least partially. The dose of ambrisentan used in this study was 0.5 mg/kg/day, which is allometrically equivalent to 35 mg per day in humans.

SUMMARY

The inventors have found that certain types of acute renal failure can be prevented and treated by administering selective ETR-A antagonists in amounts that block the endothelin receptor subtype A (ETR-A) and its activity in the kidney while not significantly blocking the endothelin receptor subtype B (ETR-B) in the kidney.

The inventors have further found that selective ETR-A antagonists interact with and antagonize the ETR-B when administered at doses approved for the treatment of other conditions such as pulmonary arterial hypertension. In this regard, several ETR antagonists are approved for oral administration to treat pulmonary arterial hypertension, such as ambrisentan and other compounds discussed below. Some of these, including ambrisentan, are considered selective ETR-A antagonists. However, their systemic administration in approved dosage forms, notwithstanding their selectivity for ETR-A, results in plasma levels that are substantially too high to be purely ETR-A selective and therefore ineffective in preventing and treating acute renal failure associated with renal vasoconstriction.

In particular, the formulations and methods of the present invention are intended to treat, or prevent conditions leading to acute renal failure due to vasoconstriction including Hepatorenal Disorders such as Hepatorenal Syndrome, Refractory Ascites and Dilutional Hyponatremia; treat or prevent complications from renal transplantation such as Delayed Graft Function and Calcineurin-Inhibitor Nephrotoxicity; treat or prevent complications of radiological procedures such as Contrast-Induced Acute Kidney Injury; treat or prevent renal complications of heart failure such as Cardiorenal Syndrome; treat or prevent Renal Failure associated with Solid-Organ Transplantation; and treat or prevent renal complications of cardiac surgery such as Acute Kidney Injury following Cardiac Surgery. In addition, the formulations and methods of the present invention are intended to support the diagnosis of renal failure in candidates for liver or kidney transplantation. Achieving the benefits of the present invention requires new and improved formulations for selective ETR-A antagonists and new methods for their therapeutic use. Accordingly, one objective of the present invention is to provide novel formulations of ETR-A antagonists and to provide a new medical use of ETR-A antagonists.

DESCRIPTION OF INVENTION AND EMBODIMENTS

The present invention relates to a finding that maintaining relatively low blood plasma concentrations of selective ETR-A antagonists, such as ambrisentan in a preferred embodiment, is effective to treat acute renal failure associated with renal vasoconstriction. The plasma concentrations of such ETR-A antagonists are preferably monitored because even selective ETR-A antagonists may partially antagonize ETR-B when the ETR-A are saturated with the antagonist. Because blocking the ETR-B receptor prevents vasodilation and the formation of urine, the clinical benefit provided by the ETR-A antagonist decreases or even disappears entirely if the ETR-B receptors are also significantly antagonized.

The present invention and its embodiments are discussed in greater detail below.

Definitions

"Acute Kidney Injury following Cardiac Surgery" (AKICS) is a complication occurring in the immediate post-operative period of subjects undergoing complex cardiac surgery. It is characterized by an increase in renal vascular resistance, decreased renal blood flow and decreased glomerular filtration rate.

"Amount effective to improve renal function" means that the amount of the administered compound will antagonize or block ETR-A in a subject's kidneys sufficiently to improve the subject's renal function. The "amount effective" or "effective amount" refer to an amount effective, at dosages and for periods of time necessary, to achieve the desired therapeutic or prophylactic result. Such effective amounts can be expressed in daily doses of the endothelin receptor antagonist and/or in the blood concentrations of the endothelin receptor antagonist, as is discussed herein. For Hepatorenal Disorders, in particular for Hepatorenal Syndrome, Refractory Ascites and Dilutional Hyponatremia, an effective amount is determined based on the amount necessary to achieve an increase in urinary output, increase in urinary sodium and/or a decrease in serum creatinine over a period of time. For Delayed Graft Function, an effective amount is determined based on the amount necessary to achieve an increase in the urinary volume and/or a reduction or normalization of serum creatinine or serum cystatin C in the immediate post-operative period and consequently may prevent the need for dialysis. For Contrast-Induced Acute Kidney Injury, an effective amount is determined based on the amount necessary to achieve a reduction or normalization of serum creatinine or serum cystatin C in the immediate period following the radiological procedure and consequently may prevent the need for dialysis. For Cardiorenal Syndrome, an effective amount is determined based on the amount necessary to achieve an increase in the urinary volume, urinary sodium and/or a reduction or normalization of serum creatinine or serum cystatin C and/or prevent the need for dialysis. For Acute Kidney Injury following Cardiac Surgery, an effective amount is determined based on the amount necessary to achieve a reduction or normalization of serum creatinine or serum cystatin C in the immediate post-operative period and/or prevent the need for dialysis. For Calcineurin-Inhibitor Nephrotoxicity, an effective amount is determined based on the amount necessary to achieve a reduction in systemic blood pressure and a normalization of urinary metabolic or electrolyte abnormalities. For Renal Failure associated with Solid-Organ Transplantation, an effective amount is determined based on the amount necessary to achieve a reduction or normalization of serum creatinine or serum cystatin C and/or prevent the need for dialysis in the post-transplantation period. For purposes of identifying whether a kidney suffers from vasoconstriction, an effective amount can be the same as the effective amount for treatment or prevention as described above; however, the effective amount could also be lower, as long as this amount is capable of influencing the renal function of the kidney. Such an effective amount may be determined based on the amount necessary to challenge the kidney function by blocking any endothelin induced vasoconstriction. Such amount would achieve a change in any renal function parameter which would indicate that the kidney's function is higher than that observed prior to the diagnostic procedure. Such markers include changes in renal blood flow, changes in renal vascular resistance, increase in urinary volume or urinary sodium, as well as changes in serum creatinine or serum cystatin C, for example.

"Calcineurin Inhibitor Nephrotoxicity" refers to an acute or chronic reversible renal deficit associated to the use of calcineurin inhibitors, renal vasoconstriction and characterized clinically by increased systemic blood pressure, electrolyte disturbances and hyperuricemia.

"Cardiorenal Syndrome" (CS) is a common renal complication occurring in patients with heart failure and is clinically characterized by the retention of water and sodium. Some forms of CS are characterized by an increase in renal vascular resistance, decreased renal blood flow, low urinary and sodium output and respond poorly to diuretic treatment.

"Contrast-Induced Acute Kidney Injury" (CIAKI) refers to a renal complication following the administration of iodine-based radiological contrast media, occurring most frequently in subjects with pre-existing renal failure, older subjects or subjects treated with large amounts of contrast media. CIAKI is characterized by an increase in renal vascular resistance and a decrease in glomerular filtration rate.

"Does not significantly antagonize endothelin receptor type B" means that the administered compound does not antagonize ETR-B at all or to such an extent that adverse renal effects, such as fluid retention, are not observed in a patient. When the ETR-B is significantly antagonized, the improved renal function caused by antagonizing ETR-A is not observed or even counteracted completely. Such antagonizing of ETR-B can be established by determining the concentration of endothelin in the blood. When ETR-B is not blocked by the antagonist, the endothelin concentration will be similar to before treatment. When ETR-B is blocked completely, the endothelin concentration after treatment with the antagonist will be higher than the level measured before treatment. With preferential ETR-A blockade, the endothelin concentration in the blood is at most 150% of the endothelin concentration before treatment, more preferably at most 130%, even more preferably at most 120%, and even more preferably at most 110% of the endothelin concentration before treatment. Most preferably, the endothelin concentration is the same in the blood after treatment with the selective ETR-A antagonist.

"Hepatorenal Disorders" refers to conditions characterized by progressive or rapidly progressive functional renal failure in a subject with pre-existing advanced liver failure (for example, caused by cirrhosis with or without ascites), with acute liver failure or in subjects awaiting a liver transplant. Hepatorenal Disorders include conditions such as Hepatorenal Syndrome, Refractory Ascites and Dilutional Hyponatremia.

"Improve renal function" (and variations thereof such as "improved renal function") means that a subject who receives the compounds and formulations according to the present invention shows clinical improvement in renal function. Such improvement may be associated with beneficial changes in renal function, including, for example, increased urine output, increased urinary sodium, decreased urinary endothelin, decreased serum creatinine, decreased renal vasoconstriction, decreased renal hypertension, decreased fluid retention and edema and decreased or delayed mortality. For example, patients treated according to the present invention may increase daily urine output from about 200 to 500 ml to more than one liter. For Hepatorenal Disorders, in particular for Hepatorenal Syndrome, Refractory Ascites and Dilutional Hyponatremia, improved renal function may be indicated by an increase in urinary output and urinary sodium, or a decrease in serum creatinine or serum cystatin C. For Delayed Graft Function, improved renal function may be indicated by an increase in urinary volume, reduction or normalization of serum creatinine or cystatin C and decreased urinary endothelin in the immediate post-operative period. For Contrast-Induced Acute Kidney Injury, improved renal function may be indicated by an increase in glomerular filtration rate or a decrease in serum creatinine. For Acute Kidney Injury following Cardiac Surgery, improved kidney function may be indicated by an increase in glomerular filtration rate or a decrease in serum creatinine. For Cardiorenal Syndrome, improved kidney function may be indicated by an increase in urinary water and sodium, a reduction in serum creatinine and/or an increase in glomerular filtration rate. For Calcineurin-Inhibitor Nephrotoxicity, improved kidney function may be indicated by a normalization of systemic blood pressure and/or an improvement in renal electrolyte disturbances. For Renal Failure associated with Solid-Organ Transplantation, improved kidney function may be indicated by normalization of serum creatinine or an increase in glomerular filtration rate. For purposes of identifying whether a kidney suffers from vasoconstriction, improved kidney function may be indicated by a change in any renal function parameter which would indicate that the kidney's function is higher than that observed prior to the diagnostic procedure. Such markers include changes in renal blood flow, changes in renal vascular resistance, increase in urinary volume or urinary sodium, as well as changes in serum creatinine or serum cystatin C, for example.

"Individual" or "subject" or "patient" is a mammal. Mammals include, but are not limited to, domesticated animals (for example, cows, sheep, cats, dogs, and horses), primates (for example, humans and non-human primates such as monkeys), rabbits, and rodents (for example, mice and rats). In preferred embodiments, the individual or subject is a human being.

"Liquid composition for parenteral administration" or "liquid formulation for parenteral administration" refers to a preparation which is suitable for intravenous, intraperitoneal, subcutaneous and/or intramuscular administration and in such form as to permit the biological activity of the active ingredient such as an ETR antagonist, contained therein to be effective, and which contains no additional components which are unacceptably toxic to a subject to which the formulation would be administered. These terms include both compositions that can be directly administered to a subject as well as compositions that need dilution into a conventional parenteral carrier solution. The liquid compositions for intravenous, intraperitoneal, subcutaneous or intramuscular administration may have the same ingredients in the same amounts, but compositions with different ingredients and different amounts also are contemplated.

"Renal Failure associated with Solid-Organ Transplantation" refers to a renal complication following solid-organ transplantation and characterized by an increase in renal vascular resistance and a decrease in glomerular filtration rate and/or increase in serum creatinine.

"Solid organ" refers to a mammalian organ like the liver, the heart, the lung or the kidney.

"Substantially continuous" means that the administration of the compounds and formulations according to the present invention may be constant or intermittent so long as the indicated blood levels of the ETR-A inhibitor are maintained, or the intended benefit is obtained.

"Treatment" (and variations thereof such as "treat" or "treating") as well as "prevention" (and variants thereof such as "prevent" or "preventing") refer to clinical intervention in an attempt to alter the natural course of the pathological condition of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis.

Treatment of Acute Renal Failure:

Various ETR antagonists are known, including selective ETR-A antagonists, such as, for example, sitaxentan, ambrisentan, atrasentan, BQ-123, zibotentan, bosentan, macitentan, tezosentan and darusentan. Preferred endothelin receptor antagonists are sitaxentan, ambrisentan, atrasentan, bosentan and macitentan. More preferred endothelin receptor antagonists are atrasentan, zibotentan and ambrisentan. Even more preferred endothelin receptor antagonists are atrasentan and ambrisentan. The most preferred antagonist is ambrisentan. None of these are approved for the treatment of acute renal failure associated with renal vasoconstriction. Instead, some of these are approved for or are candidates for the treatment of pulmonary arterial hypertension (PAH), or are candidates for treatment of diabetic nephropathy.

Contrary to the methods and formulations of the present invention, the approved dosage and formulations of such PAH therapeutic compounds create plasma levels that significantly antagonize renal ETR-B as well as ETR-A in subjects with acute renal failure thereby causing no effect or increased rather than decreased renal vasoconstriction, in addition to the inhibition of water excretion by the kidney. For example, ambrisentan, sold under the product name of Letairis® in the US (and Volibris® in Europe), was approved for oral administration at a dosage strength of either 5 mg or 10 mg. Plasma levels following one-time administration of Letairis® often reach 700 ng/ml, and generally are found in the range of about 350 ng/ml or 670 ng/ml for the 5 mg and 10 mg doses, respectively. Such levels are too high to be effective in treating acute renal failure and in fact are counterproductive because they may contribute to renal vasoconstriction and renal insufficiency.

With the currently approved oral dosing of ambrisentan, the blood level will increase shortly after ingestion and decrease over time, a cycle repeated with every subsequent oral administration to the subject and rendering a constant concentration difficult to achieve. Patients also may experience an initial drop in blood pressure. Even if administered orally at strengths lower than as approved for Letairis®, subjects treated would experience a loading dose effect, in other words an initial spike in blood plasma levels that may deleteriously antagonize both types of ETR.

In addition, upon daily dosing of the antagonist to a subject, the trough concentration of the antagonist, preferably ambrisentan, will increase to a level that is well above the initial (first day) dose level. Subjects, who develop acute renal failure associated with renal vasoconstriction, often suffer from liver dysfunction and sometimes also pre-existing kidney dysfunction. Because of this comorbidity, this patient population cannot metabolize administered medications effectively, resulting in a higher accumulation of the drug compared to subjects without kidney or liver impairment. Thus, the blood level of ambrisentan, when administered daily for oral administration as approved for PAH, will steadily increase over a few days to a base level that is well above the desired and effective concentration used in the present invention. These high concentrations may lead to the blockade of endothelin B receptor sites, which in turn may lead to adverse renal effects.

Also, patients with liver disease often have decreased levels of total protein in their blood, particularly albumin, which generally results in elevated levels of the freely available drug in the blood, as it is not otherwise bound to circulating protein present in the blood. Additionally, the active ingredients when administered orally in the form of tablets may be absorbed differently in the digestive tracts of different subjects, complicating the achievement of a steady blood concentration level.

For all of these reasons, when administered at the approved dosage form and strength, Letairis® and other compounds approved to treat PAH are not effective to treat acute renal failure. Moreover, use of approved PAH therapies to treat acute renal failure may be detrimental to renal function and may exacerbate renal failure.

Accordingly, the methods and formulations of the present invention contemplate the use of ETR-A antagonists to achieve much lower concentrations than would be appropriate for approved therapies of other conditions such as PAH. In addition, preferred embodiments of the present invention also involve parenteral routes of administration, particularly intravenous.

In a preferred embodiment, the invention pertains to the use of ambrisentan or a liquid composition comprising ambrisentan in the treatment of Hepatorenal Syndrome, wherein ambrisentan is administered to a treated subject such that the plasma levels of ambrisentan are maintained below about 100 ng/ml. The invention hence pertains to ambrisentan for use in treating Hepatorenal Syndrome, wherein ambrisentan is administered to a treated subject such that the plasma levels of ambrisentan are maintained below about 100 ng/ml. Further, the invention provides a method for treating a subject suffering from Hepatorenal Syndrome comprising administering intravenously ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Hepatorenal Syndrome, wherein ambrisentan is administered to a treated subject such that the plasma levels of ambrisentan are maintained below about 100 ng/ml. The invention hence pertains to ambrisentan for use in treating subjects who may be at risk of developing Hepatorenal Syndrome, wherein ambrisentan is administered to a treated subject such that the plasma levels of ambrisentan are maintained below about 100 ng/ml. Further, the invention provides a method for prophylactically treating a subject who may be at risk of developing Hepatorenal Syndrome comprising administering intravenously ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Hepatorenal Disorders, wherein ambrisentan is administered to a treated subject such that the plasma levels of ambrisentan are maintained below about 100 ng/ml. The invention hence pertains to ambrisentan for use in treating Hepatorenal Disorders, wherein ambrisentan is administered to a treated subject such that the plasma levels of ambrisentan are maintained below about 100 ng/ml. Further, the invention provides a method for treating a subject suffering from Hepatorenal Disorders comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Hepatorenal Disorders, wherein ambrisentan is administered to a treated subject such that the plasma levels of ambrisentan are maintained below about 100 ng/ml. The invention hence pertains to ambrisentan for use in treating subjects who may be at risk of developing Hepatorenal Disorders, wherein ambrisentan is administered to a treated subject such that the plasma levels of ambrisentan are maintained below about 100 ng/ml. Further, the invention provides a method for prophylactically treating a subject who may be at risk of developing Hepatorenal Disorders comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Refractory Ascites, wherein ambrisentan is administered to a treated subject such that the plasma levels of ambrisentan are maintained below about 100 ng/ml. The invention hence pertains to ambrisentan for use in treating Refractory Ascites, wherein ambrisentan is administered to a treated subject such that the plasma levels of ambrisentan are maintained below about 100 ng/ml. Further, the invention provides a method for treating a subject suffering from Refractory Ascites comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Refractory Ascites, wherein ambrisentan is administered to a treated subject such that the plasma levels of ambrisentan are maintained below about 100 ng/ml. The invention hence pertains to ambrisentan for use in treating subjects who may be at risk of developing Refractory Ascites, wherein ambrisentan is administered to a treated subject such that the plasma levels of ambrisentan are maintained below about 100 ng/ml. Further, the invention provides a method for prophylactically treating a subject who may be at risk of developing Refractory Ascites comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Dilutional Hyponatremia, wherein ambrisentan is administered to a treated subject such that the plasma levels of ambrisentan are maintained below about 100 ng/ml. The invention hence pertains to ambrisentan for use in treating Dilutional Hyponatremia, wherein ambrisentan is administered to a treated subject such that the plasma levels of ambrisentan are maintained below about 100 ng/ml. Further, the invention provides a method for treating a subject suffering from Dilutional Hyponatremia comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Dilutional Hyponatremia, wherein ambrisentan is administered to a treated subject such that the plasma levels of ambrisentan are maintained below about 100 ng/ml. The invention hence pertains to ambrisentan for use in treating subjects who may be at risk of developing Dilutional Hyponatremia, wherein ambrisentan is administered to a treated subject such that the plasma levels of ambrisentan are maintained below about 100 ng/ml. Further, the invention provides a method for prophylactically treating a subject who may be at risk of developing Dilutional Hyponatremia comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Delayed Graft Function, wherein ambrisentan is administered to a treated subject such that the plasma levels of ambrisentan are maintained below about 100 ng/ml. The invention hence pertains to ambrisentan for use in treating Delayed Graft Function, wherein ambrisentan is administered to a treated subject such that the plasma levels of ambrisentan are maintained below about 100 ng/ml. Further, the invention provides a method for treating a subject suffering from Delayed Graft Function comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Delayed Graft Function following renal transplantation, wherein ambrisentan is administered to a treated subject such that the plasma levels of ambrisentan are maintained below about 100 ng/ml. The invention hence pertains to ambrisentan for use in treating subjects who may be at risk of developing Delayed Graft Function following renal transplantation, wherein ambrisentan is administered to a treated subject such that the plasma levels of ambrisentan are maintained below about 100 ng/ml. Further, the invention provides a method for prophylactically treating a subject who may develop Delayed Graft Function following renal transplantation comprising administering parenterally, preferably intravenously, ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Renal Failure associated with Solid-Organ Transplantation, wherein ambrisentan is administered to a treated subject such that the plasma levels of ambrisentan are maintained below about 100 ng/ml. The invention hence pertains to ambrisentan for use in treating Renal Failure associated with Solid-Organ Transplantation, wherein ambrisentan is administered to a treated subject such that the plasma levels of ambrisentan are maintained below about 100 ng/ml. Further, the invention provides a method for treating a subject suffering from Renal Failure associated with Solid-Organ Transplantation comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Renal Failure associated with Solid-Organ Transplantation, wherein ambrisentan is administered to a treated subject such that the plasma levels of ambrisentan are maintained below about 100 ng/ml. The invention hence pertains to ambrisentan for use in treating subjects who may be at risk of developing Renal Failure associated with Solid-Organ Transplantation, wherein ambrisentan is administered to a treated subject such that the plasma levels of ambrisentan are maintained below about 100 ng/ml. Further, the invention provides a method for prophylactically treating a subject who may develop Renal Failure associated with Solid-Organ Transplantation comprising administering parenterally, preferably intravenously, ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Calcineurin-Inhibitor Nephrotoxicity, wherein ambrisentan is administered to a treated subject such that the plasma levels of ambrisentan are maintained below about 100 ng/ml. The invention hence pertains to ambrisentan for use in treating Calcineurin-Inhibitor Nephrotoxicity, wherein ambrisentan is administered to a treated subject such that the plasma levels of ambrisentan are maintained below about 100 ng/ml. Further, the invention provides a method for treating a subject suffering from Calcineurin-Inhibitor Nephrotoxicity comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Calcineurin-Inhibitor Nephrotoxicity, wherein ambrisentan is administered to a treated subject such that the plasma levels of ambrisentan are maintained below about 100 ng/ml. The invention hence pertains to ambrisentan for use in treating subjects who may be at risk of developing Calcineurin-Inhibitor Nephrotoxicity, wherein ambrisentan is administered to a treated subject such that the plasma levels of ambrisentan are maintained below about 100 ng/ml. Further, the invention provides a method for prophylactically treating a subject who may be at risk of developing Calcineurin-Inhibitor Nephrotoxicity comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Contrast-Induced Acute Kidney Injury, wherein ambrisentan is administered to a treated subject such that the plasma levels of ambrisentan are maintained below about 100 ng/ml. The invention hence pertains to ambrisentan for use in treating Contrast-Induced Acute Kidney Injury, wherein ambrisentan is administered to a treated subject such that the plasma levels of ambrisentan are maintained below about 100 ng/ml. Further, the invention provides a method for treating a subject suffering from Contrast-Induced Acute Kidney Injury comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Contrast-Induced Acute Kidney Injury, wherein ambrisentan is administered to a treated subject such that the plasma levels of ambrisentan are maintained below about 100 ng/ml. The invention hence pertains to ambrisentan for use in treating subjects who may be at risk of developing Contrast-Induced Acute Kidney Injury, wherein ambrisentan is administered to a treated subject such that the plasma levels of ambrisentan are maintained below about 100 ng/ml. Further, the invention provides a method for prophylactically treating a subject who may be at risk of developing Contrast-Induced Acute Kidney Injury comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Cardiorenal Syndrome, wherein ambrisentan is administered to a treated subject such that the plasma levels of ambrisentan are maintained below about 100 ng/ml. The invention hence pertains to ambrisentan for use in treating Cardiorenal Syndrome, wherein ambrisentan is administered to a treated subject such that the plasma levels of ambrisentan are maintained below about 100 ng/ml. Further, the invention provides a method for treating a subject suffering from Cardiorenal Syndrome comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Cardiorenal Syndrome, wherein ambrisentan is administered to a treated subject such that the plasma levels of ambrisentan are maintained below about 100 ng/ml. The invention hence pertains to ambrisentan for use in treating subjects who may be at risk of developing Cardiorenal Syndrome, wherein ambrisentan is administered to a treated subject such that the plasma levels of ambrisentan are maintained below about 100 ng/ml. Further, the invention provides a method for prophylactically treating a subject who may be at risk of developing Cardiorenal Syndrome comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the treatment of Acute Kidney Injury following Cardiac Surgery, wherein ambrisentan is administered to a treated subject such that the plasma levels of ambrisentan are maintained below about 100 ng/ml. The invention hence pertains to ambrisentan for use in treating Acute Kidney Injury following Cardiac Surgery, wherein ambrisentan is administered to a treated subject such that the plasma levels of ambrisentan are maintained below about 100 ng/ml. Further, the invention provides a method for treating a subject suffering from Acute Kidney Injury following Cardiac Surgery comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

In a preferred embodiment, the invention pertains to the use of ambrisentan or a liquid composition comprising ambrisentan in the prevention of Acute Kidney Injury following Cardiac Surgery, wherein ambrisentan is administered to a treated subject such that the plasma levels of ambrisentan are maintained below about 100 ng/ml. The invention hence pertains to ambrisentan for use in treating subjects who may be at risk of developing Acute Kidney Injury following Cardiac Surgery, wherein ambrisentan is administered to a treated subject such that the plasma levels of ambrisentan are maintained below about 100 ng/ml. Further, the invention provides a method for prophylactically treating a subject who may be at risk of developing Acute Kidney Injury following Cardiac Surgery comprising administering parenterally ambrisentan or a liquid composition comprising ambrisentan wherein an effective amount of ambrisentan is administered to the subject, wherein ambrisentan is administered to a treated subject such that the plasma levels of ambrisentan are maintained below about 100 ng/ml.

The invention further pertains to ambrisentan for use in the treatment of a subject to identify a reduced renal function due to vasoconstriction, wherein ambrisentan is administered to a treated subject such that the plasma levels of ambrisentan are maintained below about 100 ng/ml. Preferably, the invention pertains to ambrisentan for use in the treatment of a subject to identify whether a reduction in renal function is due to renal vasoconstriction, wherein ambrisentan is administered to a subject such that the plasma levels of ambrisentan are maintained below about 100 ng/ml. Further, the invention provides a method for treating a subject and identifying a reduced renal function due to vasoconstriction comprising administering intravenously ambrisentan or a liquid composition comprising ambrisentan wherein an effective amount of ambrisentan is administered to the subject, and wherein the renal function is determined before and after treatment, wherein ambrisentan is administered to a treated subject such that the plasma levels of ambrisentan are maintained below about 100 ng/ml.

The invention further pertains to ambrisentan for use in the treatment of a subject to identify a reduced renal function, wherein ambrisentan is administered to a treated subject such that the plasma levels of ambrisentan are maintained below about 100 ng/ml. Preferably, the invention pertains to ambrisentan for use in the treatment of a subject to identify whether renal function is reduced, wherein ambrisentan is administered to a subject such that the plasma levels of ambrisentan are maintained below about 100 ng/ml. Further, the invention provides a method for treating a subject and identifying a reduced renal function comprising administering intravenously ambrisentan or a liquid composition comprising ambrisentan wherein an effective amount of ambrisentan is administered to the subject, and wherein the renal function is determined before and after treatment, wherein ambrisentan is administered to a treated subject such that the plasma levels of ambrisentan are maintained below about 100 ng/ml. At present, it is difficult to assess whether a kidney suffers from a reduced renal function due to vasoconstriction. Conventionally, such assessments are conducted broadly by performing a biopsy, which is invasive, is not without risk for a patient and does not always provide a successful assessment. The present use and method is non-invasive, easy to apply and poses relatively low risk to the patient. The present method and use can replace or complement biopsies. The method and use of the invention serve to identify whether kidneys are impaired by conditions, e.g. by severe liver damage, leading to vasoconstriction to and/or in the kidneys, and whether the renal function of those kidneys could recover to its original or to an improved renal function, either by itself or by treatment with ambrisentan.

The invention further pertains to ambrisentan for use in the treatment of a subject suffering from a hepatorenal disorder, and to identify a reduced renal function due to vasoconstriction, wherein ambrisentan is administered to a treated subject such that the plasma levels of ambrisentan are maintained below about 100 ng/ml. Preferably, the invention pertains to ambrisentan for use in the treatment of a subject suffering from a Hepatorenal Disorder, and to identify whether a reduction in renal function is due to renal vasoconstriction, wherein ambrisentan is administered to a treated subject such that the plasma levels of ambrisentan are maintained below about 100 ng/ml. Further, the invention provides a method for treating a subject suffering from Hepatorenal Disorder, and identifying a reduced renal function due to vasoconstriction comprising administering intravenously ambrisentan or a liquid composition comprising ambrisentan wherein an effective amount of ambrisentan is administered to the subject, and wherein the renal function is determined before and after treatment, wherein ambrisentan is administered to a treated subject such that the plasma levels of ambrisentan are maintained below about 100 ng/ml.

The invention further pertains to ambrisentan for use in the treatment of a subject awaiting a liver transplant and to identify a reduced renal function, wherein ambrisentan is administered to a treated subject such that the plasma levels of ambrisentan are maintained below about 100 ng/ml. Preferably, the invention pertains to ambrisentan for use in the treatment of a subject awaiting a liver transplant and to identify a reduction in renal function, wherein ambrisentan is administered to a treated subject such that the plasma levels of ambrisentan are maintained below about 100 ng/ml. Further, the invention provides a method for treating a subject awaiting a liver transplant and identifying a reduced renal function comprising administering intravenously ambrisentan or a liquid composition comprising ambrisentan wherein an effective amount of ambrisentan is administered to the subject, and wherein the renal function is determined before and after treatment, wherein ambrisentan is administered to a treated subject such that the plasma levels of ambrisentan are maintained below about 100 ng/ml.

The invention further pertains to ambrisentan for use in the treatment of a subject awaiting a liver transplant and in the absence of an improvement of renal function in the subject, the subject is eligible for a dual liver-kidney transplant, preferably the kidney will be transplanted into the subject, wherein ambrisentan is administered to a treated subject such that the plasma levels of ambrisentan are maintained below about 100 ng/ml. Preferably, the invention pertains to ambrisentan for use in the treatment of a subject awaiting a liver transplant in the absence of an improvement of renal function in the subject, the subject is eligible for a dual liver-kidney transplant, preferably the kidney will be transplanted into the subject, wherein ambrisentan is administered to a treated subject such that the plasma levels of ambrisentan are maintained below about 100 ng/ml. Further, the invention provides a method for treating a subject awaiting a liver transplant and identifying a reduced renal function comprising administering intravenously ambrisentan or a liquid composition comprising ambrisentan wherein an effective amount of ambrisentan is administered to the subject, and wherein the renal function is determined before and after treatment, and in the absence of an improvement of renal function in the subject, the subject is eligible for a dual liver-kidney transplant, preferably the kidney will be transplanted into the subject, wherein ambrisentan is administered to a treated subject such that the plasma levels of ambrisentan are maintained below about 100 ng/ml. The method and use of the invention provides the surgeon and/or medical team performing the liver transplant an easy and non-invasive method to decide whether a kidney transplant is also necessary, or whether the kidney has a reasonable chance to retain its original or obtain an acceptable and improved renal function after the liver transplant.

The invention further pertains to ambrisentan for use in the treatment of a subject, who has previously received a renal transplant, and to identify a reduced renal function, wherein ambrisentan is administered to a treated subject such that the plasma levels of ambrisentan are maintained below about 100 ng/ml. Preferably, the invention pertains to ambrisentan for use in the treatment of a subject, who has previously received a renal transplant, and to identify a reduction in renal function, wherein ambrisentan is administered to a treated subject such that the plasma levels of ambrisentan are maintained below about 100 ng/ml. Further, the invention provides a method for treating a subject, who has previously received a renal transplant, and identifying a reduced renal function comprising administering intravenously ambrisentan or a liquid composition comprising ambrisentan wherein an effective amount of ambrisentan is administered to the subject, and wherein the renal function is determined before and after treatment, wherein ambrisentan is administered to a treated subject such that the plasma levels of ambrisentan are maintained below about 100 ng/ml. This method and use of the invention may allow a medical practitioner to judge and decide whether further treatment with ambrisentan is required in order to improve the chances of success of the renal transplant.

The above embodiments also apply to zibotentan and atrasentan, and their individual embodiments are also included.

Therapeutic Levels of ETR-A Antagonist:

In a preferred embodiment of the present invention, the ETR-A antagonist is ambrisentan. For purposes of the present invention, ambrisentan is administered to a treated subject such that the plasma levels of that compound preferably are maintained below about 100 ng/ml, preferably below about 75 ng/ml, more preferably below about 50 ng/ml, even more preferably below about 40 ng/ml, even more preferably below about 25 ng/ml, and most preferably below about 20 ng/ml, and generally, the plasma level of ambrisentan is at least 0.1 ng/ml, preferably at least 0.2 ng/ml more preferably at least 0.3 ng/ml, even more preferably at least 0.5 ng/ml, even more preferably at least 1 ng/ml, and most preferably at least 5 ng/ml. The said plasma levels of ambrisentan refer to the overall ambrisentan concentration in the blood plasma, which include both the ambrisentan bound to proteins present in the blood and the free, non-bound ambrisentan present in the blood. The plasma levels or concentration of both bound and non-bound ambrisentan can be determined using conventional techniques.

In a further embodiment, ambrisentan is administered to a treated subject such that the plasma levels of free ambrisentan (i.e. not bound to protein) are at most 1 ng/ml, preferably at most 0.8 ng/ml, more preferably at most 0.5 ng/ml, even more preferably at most 0.4 ng/ml and most preferably at most 0.2 ng/ml, and generally at least 0.001 ng/ml, preferably at least 0.005 ng/ml, more preferably at least 0.01 ng/ml, even more preferably at least 0.05 ng/ml, and most preferably at least 0.1 ng/ml. The plasma levels or concentration of the free ambrisentan in the blood plasma can be determined by separating the ambrisentan bound to protein and determining the ambrisentan concentration using conventional analytical techniques.

In one embodiment of the invention, the rate of administration of the ETR-A antagonist, preferably ambrisentan, is equal or substantially equal to the rate at which the antagonist, preferably ambrisentan is eliminated from the blood. In this way, the concentration of the antagonist in the blood plasma does not accumulate as opposed to accumulation observed during the treatment of PAH as indicated above. The elimination of for example ambrisentan proceeds through the kidney and/or the liver of the subject, and the elimination speed will depend on the blood plasma concentration of ambrisentan.

Administration Protocols:

It is contemplated that ETR-A antagonists according to the present invention will be administered for a period of time in which such administration improves renal function and provides clinical benefit. In the case the ETR-A antagonist, in particular ambrisentan, is used to treat acute kidney failure which is of a temporary nature, e.g. treating DGF or Calcineurin-Inhibitor Nephrotoxicity, the ETR-A antagonist will be administered for a period of time of up to about fourteen days, preferably up to about ten days, more preferably for about three to five days and most preferably for about four days. And the administration of the ETR-A antagonist, when administered intravenously, will be substantially continuous.

However, a physician may choose to administer the ETR-A antagonist in a repeated cycle of, for example, four days, with one or more intervening days in which the compound is not administered.

In the case the ETR-A antagonist, in particular ambrisentan, is used to treat kidney failure which may be persistent, e.g. treating Hepatorenal Disorders or cardiorenal syndrome, the ETR-A antagonist will be administered for a prolonged period of time on a daily basis. The prolonged period can be the period up to, during and/or after a solid organ transplant, e.g. of a kidney or of a liver, or the treatment can be prolonged until the patient dies.

Formulations:

A preferred formulation of the ETR-A antagonist, preferably ambrisentan, according to the invention is intravenous. Other forms of parenteral administration also are contemplated, such as subcutaneous, trans-dermal, intraperitoneal and intramuscular. Of these forms, subcutaneous is preferred. Doses that are not administered orally have the additional advantage of being appropriate for subjects who are unable to swallow, such as subjects suffering from a neurological deficit or hepatic encephalopathy or those subjects under anesthesia or similar conditions. Parenteral administration has the advantage that the antagonist is more effective in a shorter period of time than alternative administration methods, and the desired blood concentration can be reached readily. Additionally, the dose can be adjusted in a simple manner, which may be necessary in view of the metabolic and functional characteristics of the subject.

The present invention further pertains to a liquid composition for parenteral administration comprising an endothelin receptor antagonist, a buffer and a solvent. Preferably, the invention pertains to a liquid composition for parenteral administration comprising ambrisentan, a buffer and a solvent.

The liquid composition of the invention is preferably substantially free of particles. More preferably, the liquid composition of the invention is free of particles. With "particles" is meant any kind of solids including particles of the endothelin receptor antagonist, dust particles or polymeric particles. The term "substantially free of particles" refers to solid particles being present in amounts and sizes as prescribed in the Pharmacopeia and acceptable according to regulatory standards.

The liquid composition of the invention may be lyophilized.

In one embodiment of the invention, the liquid compositions comprise the endothelin receptor antagonist, preferably ambrisentan, in an amount of at most 15% by weight (wt %), based on the total weight of the liquid composition. Preferably, the endothelin receptor antagonist, preferably ambrisentan, is present in an amount of at most 10 wt %, more preferably at most 5 wt %, even more preferably at most 2 wt % and most preferably at most 1 wt %, and preferably at least 0.0001 wt %, more preferably at least 0.001 wt %, even more preferably at least 0.005 wt % and most preferably at least 0.01 wt %, based on the total weight of the liquid composition.

In one embodiment of the invention, the liquid composition comprises the buffer in an amount of at most 15% by weight (wt %), based on the total weight of the liquid composition. Preferably, the buffer is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the liquid composition.

Suitable solvents for use in the compositions of the invention include water, alcohols such as ethanol, glycerin, polyethylene glycol such as PEG300, PEG400 and PEG600; propylene glycol, N-methyl-2-pyrrolidone, and combinations of two or more of these solvents. Of these solvents water, ethanol, propylene glycol and polyethylene glycol or combinations comprising predominantly any one of these solvents are preferred. In another preferred embodiment, the composition of the invention does not contain water as solvent, and more preferably the composition is free from water.

In one embodiment of the invention, the liquid composition comprises the solvent in an amount of at least 85% by weight (wt %), based on the total weight of the liquid composition. Preferably, the solvent is present in an amount of at least 90 wt % and most preferably at least 92 wt %, and preferably at most 99.9 wt %, more preferably at most 98 wt %, and most preferably at most 95 wt %, based on the total weight of the liquid composition. Typically, the total amount of the endothelin receptor antagonist, the buffer, the solvent and additional excipients (when present) add up to 100 wt % in the liquid compositions of the invention.

When a buffer is present in the liquid composition, the buffer used in the composition of the invention may be any buffer known in the art which can be suitably used for parenteral administration. The buffer generally serves to maintain the composition at a constant pH, in particular upon storage and when the composition is moderately diluted. In one embodiment of the invention, the buffer is chosen such that the pH of the composition is generally between 6 and 12, preferably the pH is at least 6.5, more preferably at least 7, and preferably the pH is at most 10, and more preferably at most 9. Particularly preferred are compositions comprising ambrisentan having a pH of at least 9, as these compositions typically have a better stability and may have a higher concentration of ambrisentan.

In an embodiment of the invention, the pH of the resulting parenteral composition after adding the concentrated liquid composition of the invention is generally between 6 and 12, preferably the pH is at least 6.5, more preferably at least 7, and preferably the pH is at most 9, and more preferably at most 8.

Examples of suitable buffers include ammonium acetate, arginine, sodium benzoate, disodium citrate, trisodium citrate, diethanol amine, hydrobromic acid, monoethanol amine, phosphoric acid, monobasic sodium phosphate, dibasic sodium phosphate, tribasic sodium phosphate, monobasic potassium phosphate, dibasic potassium phosphate, tris (hydroxymethyl)methylamine (Tromethamine or Tris), 4-2-hydroxyethyl-1-piperazineethanesulfonic acid (HEPES), and 2(R)-2-(methylamino)succinic acid, and combinations of two or more of said buffers. It is also contemplated to combine one or more of the mentioned buffers with one or more buffer agents having a pKa below 6 and above 10 as long as the overall pH of the composition of the invention is between 6 and 10.

The liquid composition may be comprised of other components commonly used in liquid compositions for parenteral administration. When the liquid formulation of the invention comprises components other than the endothelin receptor antagonist or ambrisentan, the buffer and the solvent, the total amount of the endothelin receptor antagonist or ambrisentan, the buffer, the solvent, and the other components, such as excipients, add up to 100 wt % of the total weight of the liquid composition.

The compositions of the invention may further comprise excipients. Suitable excipients are known in the art. Such excipients include, stabilizers and/or bulking agents such as mannitol, sucrose, trehalose, polyethylene glycol; tonicity agents like dextrose, sodium chloride, glycerol, glycerin and mannitol; viscosity enhancers or reducers such as sodium carboxymethyl cellulose, acacia, gelatin, methyl cellulose and polyvinyl pyrrolidone; surfactants like polyoxyethylene sorbitan monooleate (Tween 80), sorbitan monooleate, polyoxyethylene sorbitan monolaurate (Tween 20), polyoxyethylene polyoxypropylene copolymers (Pluronics), and lecithin; chelates like calcium disodium ethylenediaminetetra acetic acid (EDTA), disodium EDTA, sodium EDTA, calcium versetamide Na, calteridol and diethylenetriaminepenta acetic acid (DTPA); antioxidants such as acetyl cysteine, sulfurous acid salts (bisulfites and metasulfites), antimicrobial agents like phenol, meta-cresol, benzyl alcohol, methyl paraben, propyl paraben and butyl paraben; and other adjuvants. It is appreciated that some excipients may have multiple properties.

In one embodiment of the invention, the liquid composition comprises the excipient in an amount of at most 15% by weight (wt %), based on the total weight of the liquid composition. Preferably, the buffer is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the liquid composition.

In a preferred embodiment, the liquid composition of the invention is isotonic. In a preferred embodiment, the liquid composition of the invention is sterile.

The liquid compositions of the invention can be prepared using conventional techniques. Typically, the invention pertains to a process for preparing a liquid composition comprising the steps of (a) contacting the endothelin receptor antagonist, preferably ambrisentan, the buffer and the solvent and optionally the excipient and (b) stirring the solution to allow dissolution of the various ingredients, in particular the endothelin receptor antagonist or ambrisentan; and (c) subsequently sterilizing the resulting solution. Step (a) of the process of the invention may comprise of contacting all ingredients at once or it may comprise contacting the ingredients in sequential order, whereby the one or more steps can proceed at the same temperature or at different temperatures. For example, the ingredients that easily dissolve in the solvent at room temperature can be contacted at room temperature first, and subsequently the temperature can be raised, e.g. to 50° C., after which the lowly soluble compounds are added, e.g. the endothelin receptor antagonist such as ambrisentan. Step (b) may proceed until no solid particles can be discerned visually or through analytical techniques. The sterilization of step (c) of the process can be conducted using any sterilization technique known in the art such as filtration and autoclave sterilization. It has been found, however, that the use of an autoclave is generally undesirable as the endothelin receptor antagonist, especially ambrisentan, can decompose.

Liquid compositions for parenteral administration can be provided in any suitable container including but not limited to an ampoule, a vial, a pre-filled syringe, a cartridge for a subcutaneous pump, a cartridge for a subcutaneous pen, medication reservoir for a subcutaneous pump or an IV container such as an IV bag or bottle. The concentration of the ETR-A receptor antagonist may differ depending on the container used in order to achieve improved renal function and clinical benefit.

The liquid compositions may be administered directly to the subject. They also initially may be stored or formulated in concentrated forms that will be diluted in an appropriate parenteral solution, such as conventional physiological solutions for intravenous administration, before being administered. Appropriate buffers, excipients and preservatives are conventional. Examples of such parenteral solutions include saline solutions (sterile aqueous solutions of sodium chloride), Ringer's lactate solution, Hartmann's solution (comprising sodium lactate), dextrose-containing solutions (like D5W or D10W) and solutions combining any of the foregoing ingredients (like D5NS or D5LR).

The liquid compositions may be added to the conventional parenteral solutions using conventional techniques. The dilution factor of the endothelin receptor antagonist may be at least 5, which means that, for example, 50 ml of the liquid composition of the invention is added to 200 ml of the conventional parenteral solutions. Preferably, the dilution factor is at least 10 and most preferably at least 15, and generally at most 100, preferably at most 75, and most preferably at most 50.

In general, it is contemplated that persons skilled in the art will adjust the amount of ETR-A (or ambrisentan) and formulation by conventional means as is appropriate for administration to a particular subject.

The above embodiments of the liquid composition of the invention also apply to zibotentan and atrasentan, and their individual embodiments are also included.

Containers Comprising ETR-A Antagonist

The liquid composition of the invention can be provided in any suitable container including but not limited to an ampoule, a vial, a pre-filled syringe, a cartridge for a subcutaneous pen, medication reservoir for a subcutaneous pump or an IV bag. The concentration of the endothelin receptor antagonist may differ depending on the container used. The invention therefore further pertains to an ampoule or vial containing the liquid composition of the invention wherein the endothelin receptor antagonist, preferably ambrisentan, is present at a concentration of typically at least 0.001 wt %, more preferably at least 0.01 wt %, even more preferably at least 0.1 wt % and most preferably at least 0.2 wt %, based on the total weight of the liquid composition, and typically at most 5 wt %, preferably at most 3 wt %, more preferably at most 2 wt %, even more preferably at most 1 wt %, and most preferably at most 0.5 wt %, based on the total weight of the liquid composition.

The invention therefore pertains to a pre-filled syringe containing the liquid composition of the invention wherein the endothelin receptor antagonist, preferably ambrisentan, is present at a concentration of typically at least 0.001 wt %, more preferably at least 0.01 wt %, even more preferably at least 0.02 wt % and most preferably at least 0.03 wt %, based on the total weight of the liquid composition, and typically at most 1 wt %, preferably at most 0.8 wt %, more preferably at most 0.6 wt %, and most preferably at most 0.5 wt %, based on the total weight of the liquid composition.

The invention therefore pertains to a cartridge for a subcutaneous pump or medication reservoir for a subcutaneous pump containing the liquid composition of the invention wherein the endothelin receptor antagonist, preferably ambrisentan, is present at a concentration of typically at least 0.001 wt %, more preferably at least 0.01 wt %, even more preferably at least 0.02 wt % and most preferably at least 0.03 wt %, based on the total weight of the liquid composition, and typically at most 1 wt %, preferably at most 0.8 wt %, more preferably at most 0.6 wt %, and most preferably at most 0.5 wt %, based on the total weight of the liquid composition.

The invention therefore pertains to a cartridge for a subcutaneous pen containing the liquid composition of the invention wherein the endothelin receptor antagonist, preferably ambrisentan, is present at a concentration of typically at least 0.001 wt %, more preferably at least 0.01 wt %, even more preferably at least 0.02 wt % and most preferably at least 0.03 wt %, based on the total weight of the liquid composition, and typically at most 1 wt %, preferably at most 0.8 wt %, more preferably at most 0.6 wt %, and most preferably at most 0.5 wt %, based on the total weight of the liquid composition.

The invention therefore pertains to an IV container (including a bag or a bottle) containing the liquid composition of the invention wherein the endothelin receptor antagonist, preferably ambrisentan, is present at a concentration of typically at least 0.00001 wt %, more preferably at least 0.0001 wt %, even more preferably at least 0.001 wt % and most preferably at least 0.002 wt %, based on the total weight of the liquid composition, and typically at most 0.05 wt %, preferably at most 0.03 wt %, more preferably at most 0.01 wt %, and most preferably at most 0.005 wt %, based on the total weight of the liquid composition.

The above embodiments for the containers also apply to zibotentan and atrasentan, and their individual embodiments are also included.

Pretreatment of Kidneys for Transplantation:

The invention further pertains to the use of the liquid composition according to the invention in the pretreatment of kidneys for kidney transplantation. The invention hence pertains to ambrisentan for use in pre-treating of kidneys in kidney transplantation. Further, the invention provides a method for pre-treating of kidneys with the liquid composition of the invention comprising the step of administering a liquid composition according to the invention comprising an effective amount of the endothelin receptor antagonist to the kidney. Preferably, the invention pertains to a method for pre-treating of kidneys with ambrisentan or a liquid composition comprising ambrisentan wherein an effective amount of ambrisentan is administered to the kidney, wherein ambrisentan is administered to a kidney such that the levels of ambrisentan in the vascular space of the kidney are maintained below about 1 ng/ml. The invention further pertains to ambrisentan for use in the pretreatment of kidneys for kidney transplantation, wherein ambrisentan is administered to a treated kidney such that the plasma levels of ambrisentan in the vascular space of the kidney are maintained below about 1 ng/ml. The pre-treated kidney can subsequently be transplanted into a subject. The liquid formulation used in the pre-treatment comprises an effective amount of the endothelin receptor antagonist, preferably ambrisentan. Such an effective amount may be achieved by flushing the kidney with a liquid composition of the invention having an antagonist concentration that is 20 to 100 times lower than the concentration of the liquid composition used to treat a patient. For example, 1 liter of a liquid composition comprising ambrisentan at a concentration in the range of 0.001 to 1 ng/ml is used to flush a kidney. By pre-treating the kidney to be transplanted with the endothelin receptor antagonist of the invention, the transplanted kidney generally has a higher chance to become more rapidly functional, a lower chance of failing in the immediate post-transplantation period, and to function in the transplant recipient longer compared to an untreated kidney. The method may further comprise the step of administering intravenously a liquid composition of the invention comprising an effective amount of the endothelin receptor antagonist to the subject. This further step may further increase the survival rate of the transplanted kidney.

The invention further pertains to the use of the liquid composition according to the invention in the preservation of harvested kidneys awaiting transplantation. The invention hence pertains to ambrisentan for use in the preservation of harvested kidneys awaiting transplantation. Further, the invention provides a method for the preservation of kidneys awaiting transplantation with the liquid composition of the invention prior to transplantation comprising the step of administering a liquid composition of the invention comprising an effective amount of the endothelin receptor antagonist to the kidney. Preferably, the invention further pertains to a method for preservation of kidneys awaiting transplantation with ambrisentan or a liquid composition comprising ambrisentan wherein an effective amount of ambrisentan is administered to the kidney, wherein ambrisentan is administered to a kidney such that the levels of ambrisentan in the vascular space of the kidney are maintained below about 1 ng/ml. The invention further pertains to ambrisentan for use in the preservation of kidneys suitable for transplantation, wherein ambrisentan is administered to a treated kidney such that the levels of ambrisentan in the vascular space of the kidney are maintained below about 1 ng/ml. The liquid formulation used in the pre-treatment comprises an effective amount of the endothelin receptor antagonist, preferably ambrisentan. By preserving the kidney to be transplanted in a solution containing the endothelin receptor antagonist of the invention, preferably ambrisentan, the transplanted kidney generally has a higher chance to become more rapidly functional, a lower chance of failing in the immediate post-transplantation period, and to function in the transplant recipient longer compared to an untreated kidney. The method may further comprise the step of administering intravenously a liquid composition of the invention comprising an effective amount of the endothelin receptor antagonist to the subject receiving the kidney. This further step may further increase the survival rate of the transplanted kidney.

In a further embodiment, ambrisentan is administered to or flushed through the kidney to be transplanted at a concentration of ambrisentan of at most 1 ng/ml, preferably at most 0.75 ng/ml, more preferably at most 0.5 ng/ml, even more preferably at most 0.4 ng/ml and most preferably at most 0.2 ng/ml, and generally at least 0.001 ng/ml, preferably at least 0.003 ng/ml, more preferably at least 0.005 ng/ml, even more preferably at least 0.01 ng/ml, and most preferably at least 0.05 ng/ml.

The above embodiments also apply to zibotentan and atrasentan, and their individual embodiments are also included.

EXAMPLES

Example 1: Preparation of Ambrisentan Solution

A liquid composition comprising 0.5 mg ambrisentan per ml of solvent was prepared. First, 4.60 g sodium acid phosphate monohydrate ($NaH_2PO_4 \cdot H_2O$), 4.73 g disodium phosphate anhydrous ($Na_2HPO_4$) and 4.80 g sodium chloride were dissolved in 1000 ml sterile distilled water (q.s.) to obtain a solution having a pH of 7.4. The resulting solution was heated to 50° C. Subsequently, 0.50 g of ambrisentan was added and the solution was stirred until the ambrisentan completely dissolved. The resulting solution was cooled and sterilized by passing the solution through a suitable filter. The resulting liquid composition is in accordance with the invention and contains 0.5 mg/ml of ambrisentan. Analyzing the resulting liquid composition showed that ambrisentan remained stable and no decomposition was observed.

Stability Tests

The liquid composition of Example 1 was tested on its stability. The tests were conducted by applying 5 ml of the solution in ampoules which are stored at different temperatures, i.e. 5° C. and 25° C. for up to 180 days in conditioned chambers. The solutions did not reveal any chemical and physical decomposition of ambrisentan.

Example 2: Preparation of Ambrisentan Formulation

A liquid composition comprising 10 mg ambrisentan per ml of solvent was prepared. First, 4.00 g polysorbate 20, 10.00 g sodium ascorbate, 1.50 g sodium chloride, 1.10 g EDTA and 9.20 g disodium phosphate anhydrous were dissolved in 1000 ml sterile distilled water (q.s.) to obtain a solution having a pH of 8.0. The resulting solution was heated to 50° C. Subsequently, 10.00 g of ambrisentan was added and the solution was stirred until the ambrisentan completely dissolved. The resulting solution was cooled and sterilized by passing the solution through a suitable filter. The resulting liquid composition is in accordance with the invention and contains 10 mg/ml of ambrisentan.

Example 3: Treatment of Porcine Kidneys with Ambrisentan-Containing Liquid Composition Following Ischemic Injury All experiments were undertaken in accordance with the Home Office animals (Scientific Procedures) Act 1986. Ten kidneys were retrieved from 5 Landrace cross female pigs weighing approximately 50 kg. Two pairs of kidneys underwent 20 minutes of warm ischaemic injury and were then flushed with 500 ml of UW solution at 4° C. and stored on ice for 18 hours. After 18 hours cold storage, kidneys were prepared and flushed with 100 ml of Ringer's solution 4° C. with or without liquid composition of Example 1 which is diluted to an ambrisentan concentration of 150 µg/l. They were then left at room temperature for 20 minutes. The remaining three pairs of kidneys were retrieved after 10 minutes of warm ischaemia and stored on ice for 6 hours. They were prepared and flushed as previously described then left at room temperature for 10 minutes before reperfusion.

Kidneys were perfused with 1 liter of diluted whole autologous heparinized blood at 38.0° C. for 6 hours to assess renal function and injury. 1000 µmol/l of creatinine (Sigma-Aldrich) was added to the circuit. In the treated kidneys the ambrisentan-containing liquid composition as described above (150 µg/l) was added to the reperfusion circuit 10 minutes before the start of reperfusion. In the control and treated kidneys after 2 h 50 min of reperfusion, endothelin-1 (Sigma-Aldrich) was added to the arterial line of reperfusion circuit to achieve a concentration of (20 pg/ml). A sample of the perfusate was taken from the renal vein during the post preservation flush. Perfusion data was recorded after 30 minutes of reperfusion then at each hour. Plasma and urine samples were taken pre-reperfusion, 30 minutes after reperfusion, then at hourly time points to measure renal function.

Renal Hemodynamics

The level of renal blood flow and intra-renal resistance was similar between groups throughout the first period of reperfusion. The level of renal blood flow fell particularly in the control group after 2 hours of reperfusion (Table 1). There was then a significant fall in the renal blood flow in the control group after the administration of endothelin. Levels also fell in the treated kidneys but to a lesser extent. Intra-renal resistance increased in both groups after the administration of ambrisentan, and the increase was less pronounced in the treated kidneys compared to the control.

TABLE 1

Renal blood flow and renal resistance

| Time | Renal blood flow (ml/min/100 g) | | Renal resistance (mmHg/min/100 g) | |
|---|---|---|---|---|
| (min) | Untreated | Treated | Untreated | Treated |
| 0 | 45 | 45 | 1.12 | 1.22 |
| 30 | 76 | 79 | 0.60 | 0.58 |
| 60 | 80 | 84 | 0.59 | 0.55 |
| 120 | 78 | 85 | 0.62 | 0.56 |
| 180 | 45 | 85 | 1.42 | 0.60 |
| 240 | 62 | 97 | 0.86 | 0.56 |
| 300 | 60 | 93 | 0.97 | 0.62 |
| 360 | 52 | 77 | 1.20 | 0.78 |

Oxygen Consumption

The levels of oxygen consumption during reperfusion was measured and tabulated in the Table below. Levels were similar between groups after 1 hour of reperfusion. At 3 hours levels were numerically lower in the control group and at 6 hours there was significant difference between the groups with lower levels in the control compared to the treated kidneys.

TABLE 2

Oxygen Consumption

| Time | Oxygen consumption (%) | |
|---|---|---|
| (h) | Untreated | Treated |
| 1 | 59 | 63 |
| 3 | 33 | 64 |
| 6 | 34 | 55 |

Urine Output

The amount of urine produced was determined in both the control and treated kidneys. The results are shown in Table 3 below. The Table demonstrates that the kidneys treated with ambrisentan exhibit a larger urine flow.

TABLE 3

Urine Flow

| Time | Urine flow (ml) | |
|---|---|---|
| (h) | Untreated | Treated |
| 0.5 | 128 | 148 |
| 1 | 65 | 124 |
| 2 | 50 | 116 |
| 3 | 24 | 80 |
| 4 | 22 | 62 |
| 5 | 14 | 44 |

Example 4: Preparation of Ambrisentan Formulation

A liquid composition comprising 5 mg ambrisentan per ml of solvent was prepared. First 300 mL Ethanol and 700 ML propylene glycol 1,2 were mixed together. The resulting solution was heated to 40° C. Subsequently, 5 g of ambrisentan was added and the solution was stirred until the ambrisentan completely dissolved. The resulting solution was cooled and sterilized by passing the solution through a suitable filter. The resulting liquid composition is in accordance with the invention and contains 5 mg/mL of ambrisentan. Analyzing the resulting liquid composition showed that ambrisentan remained stable and no decomposition was observed.

This solution obtained can be diluted in various ratios with an aqueous saline and other buffers having pH 6 and above. It is anticipated that prior to human administration, the physician will mix with sterile aqueous solution to obtain the desired ambrisentan concentration.

Stability Tests

The liquid composition of Example 4 was tested for its stability. The tests were conducted by applying 5 ml of the solution in vials which are stored at different temperatures, i.e. 5° C. and 25° C. for up to 180 days in conditioned chambers. The solutions did not reveal any chemical and physical decomposition of ambrisentan at 5° C. and some degradation was observed at 25° C.

Examples 5-10: Water-Free Ambrisentan Formulations

Various compositions in accordance with the invention and Example 4 above using a variety of solvents were prepared. To ambrisentan the solvents or solvent mixtures were added and stirred. An overview of the ingredients of these compositions are presented in the Table below.

TABLE 4

Water-free ambrisentan formulations

| Example | Solvent | Ambrisentan concentration (mg/ml) |
|---|---|---|
| 5 | Ethanol/propylen glycol 1,2 (3:7) | 1 |
| 6 | Ethanol/propylene glycol 1,2 (3:7 ) | 10 |
| 7 | Ethanol/polyethyleneglycol 300 (3:7) | 10 |
| 8 | Ethanol | 1 bis 40 |
| 9 | Prolpylene glycol 1,2 | 1 bis 10 |
| 10 | Polyethyleneglycol 300 | 1 bis 20 |

In addition to the above examples further binary and tertiary solutions can be prepared for this purpose.

The invention described in this specification generally relates to methods and formulations for the treatment and prevention of acute renal failure comprising the administration of ETR-A antagonists. While certain exemplary embodiments have been described above in detail, it is to be understood that such embodiments and examples are merely illustrative of and not restrictive of the broad invention. In particular, it should be recognized that the teachings of the invention apply to variations of the preferred embodiments that are specifically discussed. Modifications, substitutions, changes and equivalents will now occur to those skilled in the art. Thus, it will be understood that the invention is not limited to the particular embodiments or arrangements disclosed, but is rather intended to cover any changes, adaptations or modifications which are within the scope and spirit of the invention as defined by the appended claims.

Example 11: Treatment with Ambrisentan in Human Subjects

A study was performed to determine whether lower concentrations of ambrisentan in blood are less likely to produce renal side effects as those seen with current concentrations achieved with the current commercial presentation of ambrisentan. In this study a liquid composition of ambrisentan at a concentration of 5 mg/mL was administered to 20 healthy human subjects at varying rates of administration in order to achieve different ambrisentan concentrations in blood and over a period of 24 hours. Target concentrations in the low dose group were 20 and 40 ng/mL (Group A) after 4 hours and 16 hours respectively, and 80 and 160 ng/mL in the high dose group (Group B) after 4 hours and 16 hours respectively. The first target concentration of 20 and 80 ng/mL was achieved at 4 hours for Groups A and B respectively. The second target concentration of 40 and 160 ng/mL was achieved at 16 hours for Groups A and B respectively. Steady state for each target concentration was maintained for at least 8 hours prior to increasing the concentration. Ten subjects were assigned to Group A and ten subjects to Group B. Pharmacokinetic and plasma ET-1 samples were collected and analysed at different timepoints for up to 72 hours. Urine was collected for 24 hours and in intervals from 0-2 hours, 2-4 hours, 4-8 hours, 8-12, hours, 12-18 hours and 18-24 hours.

All subjects received a 100 ml/hr infusion of 0.45% physiological solution for 24 hours and ambrisentan was administered in a 250-mL solution of 0.9% of physiological solution over a period of 24 hours. Subjects had free access to water and a normal diet. At a minimum, subjects received through intravenous infusion a total of 2650 mL of water and 223.3 mmol of sodium in the 24-hour period of drug administration.

Regarding the pharmacodynamic effects of ambrisentan, the results show that at low concentrations, ambrisentan promotes diuresis by increasing urinary volume, an effect not shown at higher concentrations. In fact, concentrations above 100 ng/mL showed a significant accumulation of fluid through the inability to increase urinary output. Group A displayed a higher total urine output in 24 hours when compared to Group B, and this difference was already apparent between infusion start and the first 4 hours. The effect on urine was consistent throughout the different collection periods of the 24-hour infusion period. Patients in Group A maintained higher urinary output rates throughout the study as compared to Group B. In the Tables Below, Water Balance is the result of subtracting urine volume from intravenous liquid input.

TABLE 5

Hourly water balance

| Collection Period | Hourly Water Balance (ml/hr) | | | |
|---|---|---|---|---|
| | Group A | | Group B | |
| | Mean | SEM | Mean | SEM |
| 0 H to 2 H | −74.58 | 39.70 | −6.33 | 23.29 |
| 2 H to 4 H | −76.08 | 26.43 | 11.17 | 15.97 |
| 4 H to 8 H | −1.08 | 18.59 | 27.17 | 12.99 |
| 8 H to 12 H | −12.58 | 18.33 | 7.17 | 12.53 |
| 12 H to 18 H | −13.75 | 17.81 | −10.08 | 14.04 |
| 18 H to 24 H | −32.92 | 18.12 | 34.75 | 11.18 |

SEM: standard error of the mean

TABLE 6

Cumulative water balance

| End of Collection | Cumulative Water Balance (ml) | | | |
|---|---|---|---|---|
| | Group A | | Group B | |
| | Mean | SEM | Mean | SEM |
| 2 H | −149.17 | 79.40 | −12.67 | 46.58 |
| 4 H | −301.33 | 110.93 | 9.67 | 65.96 |
| 8 H | −305.67 | 173.33 | 118.33 | 108.69 |
| 12 H | −356.00 | 228.28 | 147.00 | 122.80 |
| 18 H | −438.50 | 302.26 | 86.50 | 155.96 |
| 24 H | −636.00 | 297.23 | 295.00 | 140.19 |

SEM: standard error of the mean

Figure 1:
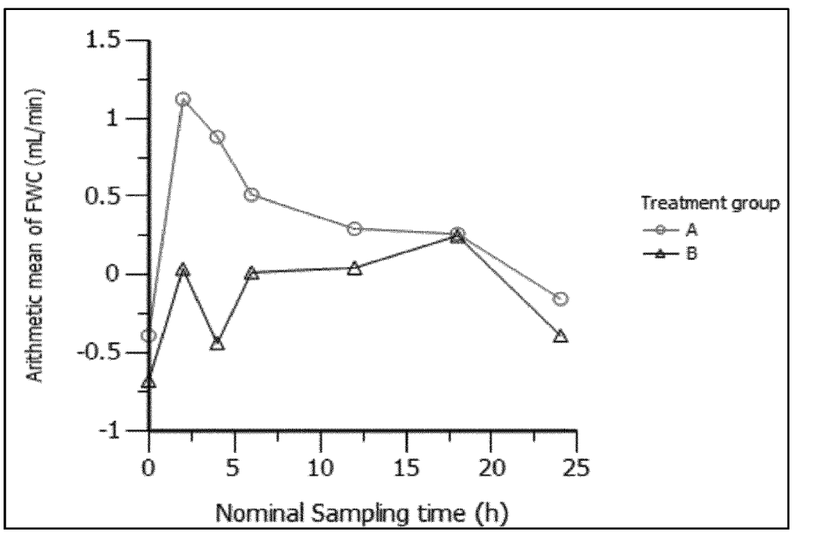
FIG. 1 depicts the free water clearance (FWC) over time of healthy patients treated with low dose of ambrisentan (Group A) and a high dose of ambrisentan (Group B).

The increase in urine formation (diuresis) was further characterised by determining the effect of ambrisentan on urine composition, specifically urine osmolality. Free water clearance (FWC), that is the proportion of urine devoid of solutes and as determined by the formula of Edelman, was higher in Group A than in Group B. This further supports the finding that concentrations of ambrisentan achieved in Group A promoted the formation of urine while those concentrations achieved in Group B tended to suppress the formation of urine. Given the significant amount of hypotonic solution administered intravenously to subjects, free water clearance was considered impaired in Group B as it remained near or below zero, as shown in FIG. 1.

Finally, the effect of the different concentrations of ambrisentan on the ETB receptor blockade was determined by measuring plasma endothelin-1 at different timepoints of the study. A steady increase in endothelin-1 was observed in the higher dose group (Group B) reaching up to more than 50% from baseline endothelin levels. A smaller increase in endothelin was observed in Group A, but this increase was not considered significant.

In conclusion, concentrations of total ambrisentan of about 100 ng/mL and higher show an adverse renal effect by promoting fluid retention. Concentrations of total ambrisentan lower than 100 ng/mL have less of an effect on fluid retention. Concentrations below 20 ng/mL show a diuretic effect, predominantly in the clearance of free water. Higher concentrations of total ambrisentan above 100 ng/mL increase plasma endothelin-1 through blockade of the ETB receptor.

The invention claimed is:

1. A method for treating a subject suffering from Calcineurin-Inhibitor Nephrotoxicity comprising administering an effective amount of ambrisentan to the subject, wherein ambrisentan is administered to the subject such that the plasma levels of ambrisentan are maintained below about 100 ng/ml, to treat the subject suffering from Calcineurin-Inhibitor Nephrotoxicity.

2. A method for prophylactically treating a subject who may develop Calcineurin-Inhibitor Nephrotoxicity comprising administering an effective amount of ambrisentan to the subject, wherein ambrisentan is administered to the subject such that the plasma levels of ambrisentan are maintained below about 100 ng/ml, to prophylactically treat the subject who may develop Calcineurin-Inhibitor Nephrotoxicity.

3. A method for treating a subject suffering from Delayed Graft Function comprising administering an effective amount of ambrisentan to the subject, wherein ambrisentan is administered to the subject such that the plasma levels of ambrisentan are maintained below about 100 ng/ml, to treat the subject suffering from Delayed Graft Function.

4. A method for prophylactically treating a subject who may develop Delayed Graft Function following renal transplantation comprising administering an effective amount of ambrisentan to the subject, wherein ambrisentan is administered to the subject such that the plasma levels of ambrisentan are maintained below about 100 ng/ml, to prophylactically treat the subject who may develop Delayed Graft Function following renal transplantation.

5. A method for treating a subject suffering from Renal Failure associated with Solid-Organ Transplantation comprising administering an effective amount of ambrisentan to the subject, wherein ambrisentan is administered to the subject such that the plasma levels of ambrisentan are maintained below about 100 ng/ml, to treat the subject suffering from Renal Failure associated with Solid-Organ Transplantation.

6. A method for prophylactically treating a subject who may develop Renal Failure associated with Solid-Organ Transplantation comprising administering an effective amount of ambrisentan to the subject, wherein ambrisentan is administered to the subject such that the plasma levels of ambrisentan are maintained below about 100 ng/ml, to prophylactically treat the subject who may develop Renal Failure associated with Solid-Organ Transplantation.

7. A method for treating a subject suffering from Cardiorenal Syndrome comprising administering an effective amount of ambrisentan to the subject, wherein ambrisentan is administered to the subject such that the plasma levels of ambrisentan are maintained below about 100 ng/ml, to treat the subject suffering from Cardiorenal Syndrome.

8. A method for treating a subject suffering from Acute Kidney Injury following Cardiac Surgery comprising administering an effective amount of ambrisentan to the subject, wherein ambrisentan is administered to the subject such that the plasma levels of ambrisentan are maintained below about 100 ng/ml, to treat the subject suffering from Acute Kidney Injury following Cardiac Surgery.

9. A method for prophylactically treating a subject who may be at risk of developing Acute Kidney Injury following Cardiac Surgery comprising administering an effective amount of ambrisentan to the subject, wherein ambrisentan is administered to the subject such that the plasma levels of ambrisentan are maintained below about 100 ng/ml, to prophylactically treat the subject who may be at risk of developing Acute Kidney Injury following Cardiac Surgery.

10. A method for treating a subject suffering from Contrast-Induced Acute Kidney Injury comprising administering an effective amount of ambrisentan to the subject, wherein ambrisentan is administered to the subject such that the plasma levels of ambrisentan are maintained below about 100 ng/ml, to treat the subject suffering from Contrast-Induced Acute Kidney Injury.

11. A method for prophylactically treating a subject who may be at risk of developing Contrast-Induced Acute Kidney Injury comprising administering an effective amount of ambrisentan to the subject, wherein ambrisentan is administered to the subject such that the plasma levels of ambrisentan are maintained below about 100 ng/ml, to prophylactically treat the subject who may be at risk of developing Contrast-Induced Acute Kidney Injury.

12. A method for treating a subject and identifying reduced renal function due to vasoconstriction comprising administering an effective amount of ambrisentan to the subject, and wherein the renal function is determined before and after treatment, wherein ambrisentan is administered to the subject such that the plasma levels of ambrisentan are maintained below about 100 ng/ml, to treat the subject and identify reduced renal function due to vasoconstriction.

13. A method for treating a subject suffering from reduced renal function due to vasoconstriction comprising administering an effective amount of ambrisentan to the subject, wherein ambrisentan is administered to the subject such that the plasma levels of ambrisentan are maintained below about 100 ng/ml, to treat the subject suffering from reduced renal function due to vasoconstriction.

14. A method for treating a subject suffering from acute renal failure comprising administering an effective amount of ambrisentan to the subject, wherein ambrisentan is administered to the subject such that the plasma levels of ambrisentan are maintained below about 100 ng/ml, to treat the subject suffering from acute renal failure.

15. A method for treating a subject suffering from acute renal failure due to vasoconstriction comprising administering an effective amount of ambrisentan to the subject, wherein ambrisentan is administered to the subject such that the plasma levels of ambrisentan are maintained below about 100 ng/ml, to treat the subject suffering from acute renal failure due to vasoconstriction.

16. A method for treating a subject, who has previously received a renal transplant, and identifying a reduced renal function due to vasoconstriction comprising administering an effective amount of ambrisentan to the subject, and wherein the renal function is determined before and after treatment, wherein ambrisentan is administered to the subject such that the plasma levels of ambrisentan are maintained below about 100 ng/ml, to treat the subject who has previously received the renal transplant and identify the reduced renal function due to vasoconstriction.

* * * * *